United States Patent [19]

Dellacoletta

[11] Patent Number: 5,068,353

[45] Date of Patent: Nov. 26, 1991

[54] SYNTHESIS OF AROMATIC BIS(ETHER PHTHALIMIDE) COMPOUNDS

[75] Inventor: Brent A. Dellacoletta, Evansville, Ind.

[73] Assignee: General Electric Company, Pittsfield, Mass.

[21] Appl. No.: 947,909

[22] Filed: Dec. 31, 1986

[51] Int. Cl.$^5$ .......................................... C07D 209/48
[52] U.S. Cl. ..................................................... 548/461
[58] Field of Search ......................................... 548/461

[56] References Cited

U.S. PATENT DOCUMENTS

| | | | |
|---|---|---|---|
| 3,847,867 | 11/1974 | Heath et al. | 260/47 CP |
| 3,879,428 | 4/1975 | Heath et al. | 260/346.3 |
| 3,933,852 | 1/1976 | Cook et al. | 260/326 N |
| 3,957,862 | 5/1976 | Heath | 260/520 E |
| 4,116,980 | 9/1978 | Webb | 260/346.3 |
| 4,273,712 | 6/1981 | Williams, III | 260/326 N |
| 4,460,778 | 7/1984 | Brunelle | 546/304 |
| 4,513,141 | 4/1985 | Brunelle et al. | 548/476 |
| 4,554,357 | 11/1985 | Verbicky, Jr. et al. | 548/461 |
| 4,577,033 | 3/1986 | Verbicky, Jr. et al. | 548/461 |

OTHER PUBLICATIONS

*Kirk–Othmer Encyclopedia of Chemical Technology*, 2nd ed., John Wiley and Sons, Inc., New York, NY (1971) Supplemental Volume, pp. 746–755.

*The Merck Index*, 10th Ed. (M. Windholz, ed.) Merck & Co., Inc. Rahway, NJ (1983) entry #1296, p. 181.

*Primary Examiner*—Mary E. Ceperley
*Attorney, Agent, or Firm*—Rothwell, Figg, Ernst & Kurz

[57] ABSTRACT

Aromatic bis(ether phthalimide) compounds of the formula (I):

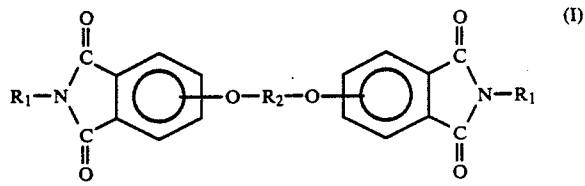

are synthesized by reacting a phthalimide of the formula (II):

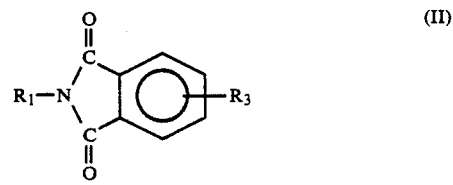

with a stoichiometric excess of an alkali metal diphenoxide salt of the formula (III):

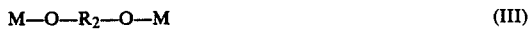

in the presence of a catalytic amount of a phase transfer catalyst, in a anhydrous nonpolar organic solvent under ether-forming conditions. Impurities are removed by solid-liquid separation techniques, such as filtering at a temperature at which the compound of formula (I) is substantially completely soluble while alkali metal salt impurities are substantially insoluble. The compound of formula (I) is recovered from the filtrate in high yields and at high purity.

31 Claims, No Drawings

SYNTHESIS OF AROMATIC BIS(ETHER PHTHALIMIDE) COMPOUNDS

TECHNICAL FIELD

This invention relates to a method of synthesizing aromatic bis(ether phthalimide) compounds, which are useful as intermediates in the synthesis of polyetherimides.

BACKGROUND OF THE INVENTION

Aromatic bis(ether phthalimide) compounds are known intermediates used in the synthesis of certain polyimides. These compounds are readily converted to the corresponding aromatic bis(ether anhydride) compounds by known methods. One example of such methods involves hydrolysis of the aromatic bis(ether phthalimide) with aqueous sodium hydroxide to produce a tetracarboxylic acid salt which is thereafter acidified to the tetracarboxylic acid, followed by dehydration of the tetracarboxylic acid to produce the aromatic bis(ether anhydride). (See U.S. Pat. No. 3,879,428.) A similar method is disclosed in U.S. Pat. No. 3,933,852, in which certain bis(N-methyl phthalimide)ethers are treated with aqueous sodium hydroxide and water to form the corresponding tetracarboxylic acid, which then is treated with, for example, glacial acetic acid and acetic anhydride to obtain the corresponding dianhydride.

The thus-derived aromatic bis(phthalic dianhydride)ethers are useful as monomers for the preparation of various polyimide homopolymers and copolymers. See, for example, *Kirk-Othmer Encyclopedia of Chemical Technology*, 2nd Ed., John Wiley and Sons, Inc., New York (1971), Supplemental Volume, pp. 746–755. U.S. Pat. No. 3,847,867 describes the production of polyetherimides by reacting certain aromatic bis(ether anhydrides) with organic diamines.

SUMMARY OF THE INVENTION

The present invention provides an improved method for synthesizing an aromatic bis(ether phthalimide) of the formula I:

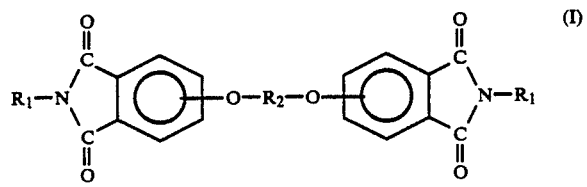

comprising reacting a phthalimide of the formula (II):

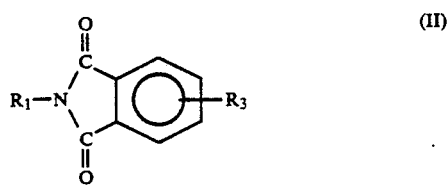

with a stoichiometric excess of an alkali metal diphenoxide salt of the formula (III):

in the presence of a catalytic amount of a phase transfer catalyst, in an anhydrous nonpolar organic solvent under ether-forming conditions. Solid-liquid separation techniques are used for removing impurities from the reaction mixture at a temperature at which the compound of formula (I) is substantially completely soluble while alkali metal salt impurities are substantially insoluble. One suitable solid-liquid separation technique is filtration at a temperature at which the compound of formula (I) is substantially completely soluble in a solvent, and passes through a filter, while alkali metal salts of impurities are insoluble and are retained on the filter. The compound of formula (I) is recovered from the filtrate in high yields and purities.

DETAILED DESCRIPTION OF THE INVENTION

The present invention provides an improved method for synthesizing an aromatic bis(ether phthalimide) of the formula (I):

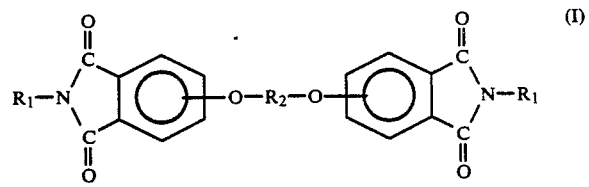

comprising reacting a phthalimide of the formula (II):

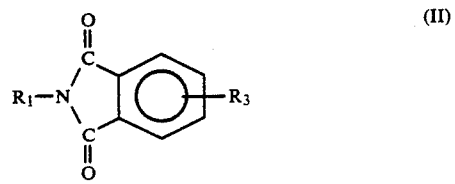

with a stoichiometric excess of an alkali metal diphenoxide salt of the formula (III):

in the presence of a catalytic amount of a phase transfer catalyst, in an anhydrous nonpolar organic solvent under ether-forming conditions. Impurities are removed by a solid-liquid separation technique, e.g., by filtering the reaction mixture at a temperature at which the compound of formula (I) is substantially completely soluble while alkali metal salt impurities are substantially insoluble. The compound of formula (I) is recovered from the liquid phase in high yields and at high purity.

$R_1$ is hydrogen or a monovalent organic radical selected from a lower alkyl group having from 1 to about 10 carbon atoms, preferably from 1 to about 5 carbon atoms; or an aromatic hydrocarbon radical, or halogenated derivative thereof, having from about 6 to about 20 carbon atoms. Radicals includes by $R_1$ are, for example, aromatic radicals such as phenyl, tolyl, xylyl, naphthyl, chlorophenyl, and bromonaphthyl, and alkyl radicals such as methyl, ethyl, and propyl groups. A particularly preferred $R_1$ group is a methyl group.

$R_2$ is a divalent organic radical which may be any alkyl or aryl group which does not interfere with the ether-forming reaction. For example, the $R_2$ group should not be so large that it causes steric hindrance of the desired reaction. The $R_2$ group also should not contain reactive groups which interfere with the desired ether-forming reaction by competition. Examples of some of the many suitable $R_2$ radicals are:

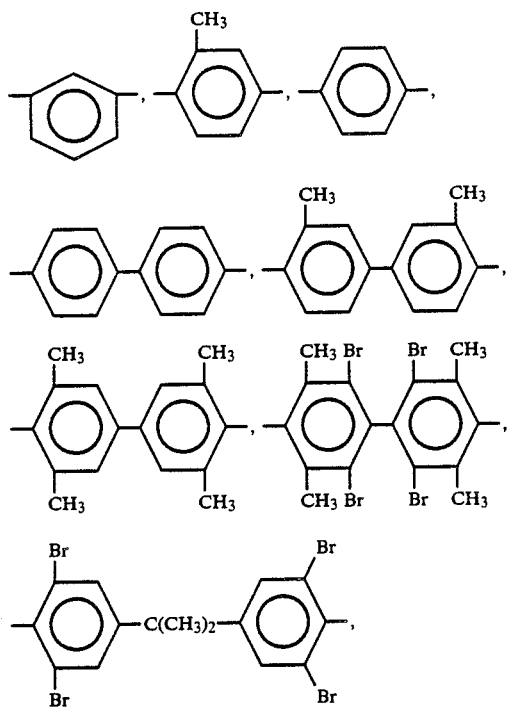

and divalent organic radicals of the general formula

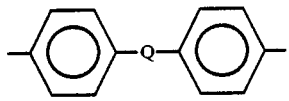

where Q represents a member selected from the class consisting of

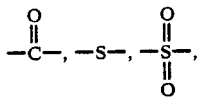

—O—, and —$C_yH_{2y}$— (where y is a whole number from 1 to about 5), and many other aromatic or straight- or branched-chain aliphatic groups.

M represents an alkali metal ion. The alkali metal ion may be, for example, sodium, potassium, or lithium, with sodium being preferred.

Compounds having the structural formula (III) are known (see, for example, U.S. Pat. Nos. 3,847,867 and 3,879,428.) Examples of some of the many compounds of formula (III) which may be used in the invention are the alkali metal salts of the following dihydric phenols:
2,2-bis(2-hydroxyphenyl)propane;
2,4'-dihydroxydiphenylmethane;
bis-(2-hydroxyphenyl)-methane;
2,2-bis-(4-hydroxyphenyl)-propane (hereinafter identified as "bisphenol-A");
1,1-bis-(4-hydroxyphenyl)-ethane;
1,1-bis-(4-hydroxyphenyl)-propane;
2,2-bis-(4-hydroxyphenyl)-pentane;
3,3-bis-(4-hydroxyphenyl)-pentane;
4,4'-dihydroxybiphenyl;
2,4'-dihydroxybenzophenone;
4,4'-dihydroxydiphenyl sulfone;
2,4'-dihydroxydiphenyl sulfone;
4,4'-dihydroxydiphenyl sulfoxide;
4,4'-dihydroxydiphenyl sulfide; etc.

A particularly preferred compound of formula (III) is bisphenol A, wherein the $R_2$ group is —$C(CH_3)_2$—. (See *The Merck Index,* 10th Ed., entry no. 1296, page 181.)

$R_3$ represents a leaving group. As used herein, "leaving group" refers to groups which are readily displaced from the starting compound of formula (II) under the ether-forming conditions of the reaction. Advantageously, $R_3$ is a nitro group (i.e., —$NO_2$) or a halide atom, such as a chloro, bromo, or fluoro substituent, preferably fluoro. The $R_3$ group may be bonded at either the 3 position or the 4 position of the benzene ring in the compound of formula (II).

Thus, in view of the different positions possible for bonding of the two oxygen atoms to the divalent radical represented by $R_2$ in the compound of formula (III), as well as the $R_3$ group of the compound of formula (II), the positions of the ether linkages in the compound of formula (I) may vary. For example, compounds of formula (I) may have ether linkages in the following positions, among others:

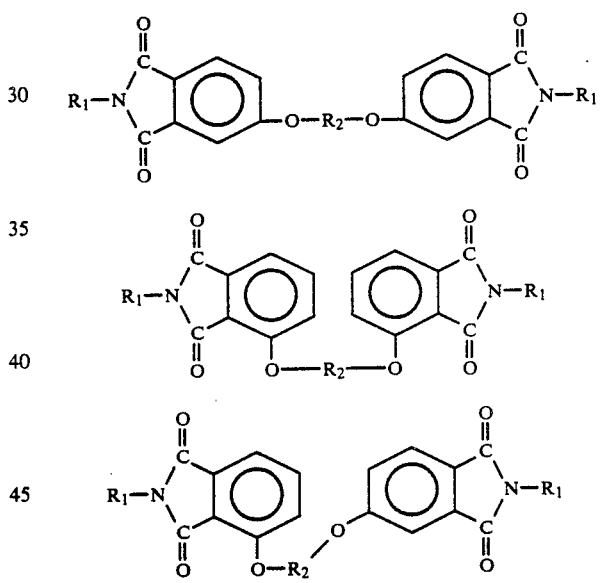

Compounds represented by formula (III) may be derived from corresponding dihydric phenol compounds having the formula HO—$R_2$—OH. These dihydric phenols generally are weakly acidic due to the phenolic hydroxyl groups. Alkali metal salts of these compounds may be prepared by known methods. (See, for example, U.S. Pat. No. 4,273,712, col. 3, lines 33-43.) Such alkali metal salts include, but are not limited to, sodium, potassium, and lithium salts. A preferred alkali metal salt for use in the present invention is a sodium salt. When the compound of formula (III) is the sodium salt of bisphenol A, the sodium salt may be prepared by mixing bisphenol A and sodium hydroxide in water, then azeotropically drying the mixture in toluene, as described in the Example below.

Phthalimide compounds of formula (II) are known. (See, for example, U.S. Pat. Nos. 4,116,980; 3,933,852 and 3,879,428.) In accordance with the invention, and the definitions of the $R_1$ and $R_3$ groups presented above, the compound of formula (II) may be, for example N-phenyl-3-nitrophthalimide, N-phenyl-4-nitrophthalimide, N-methyl-3-nitrophthalimide, N-butyl-3-chlorophthalimide, N-propyl-4-bromophthalimide, and many other such compounds.

Reactions of substituted phthalimides with dihydric phenols to form aromatic bis(ether phthalimide) compounds are known. For example, U.S. Pat. No. 3,933,852 describes the reaction of N-methyl-3-nitrophthalimide (or N-methyl-4-nitrophthalimide) with the dialkali-metal salt of bisphenol-A [(2,2-bis-4-hydroxyphenyl)propane] to form an aromatic bisimide, bisphenol A bisimide. U.S. Pat. No. 4,577,033 describes the preparation of aromatic ether imides by reaction of the disodium salt of bisphenol A with 4-nitro-N-methylphthalimide in the presence of a phase transfer catalyst. Various procedures for recovery of aromatic ether imides, produced by similar processes, are presented in U.S. Pat. No. 4,273,712. Problems encountered in the production of aromatic bis(ether phthalimide) compounds by such reactions include the presence of impurities in the reaction mixture (after completion of the reaction) which impart undesirable color to the product and negatively impact properties of the polyetherimide produced therefrom. Extraction of the reaction mixture with water or aqueous solutions has been known to result in the formation of additional highly-colored impurities.

The method described herein for production of aromatic bis(ether phthalimide) compounds is an improved process for the synthesis of such compounds. Among the advantages of the method disclosed herein is the removal of impurities, including color-forming impurities, from the reaction mixture by a solid-liquid separation step (preferably filtration) at an elevated temperature. The solid-liquid separation step optionally may be preceeded by addition of a base, such as sodium hydroxide, to the reaction mixture to form insoluble salts of certain impurities. During the solid-liquid separation step, insoluble impurities are removed, while the desired product is retained in solution. The "impurities" are compounds other than the desired product, and include those deliberately added to the reaction mixture (e.g., the reactants) as well as those formed by side reactions. The compounds present as impurities will vary according to the choice of $R_1$, $R_2$, and $R_3$ groups in the reactants. Aromatic bis(ether phthalimide) compounds synthesized according to the method disclosed herein are obtained in high yields and at a relatively high level of purity. These and other advantages of the method of the present invention are further described below.

In accordance with the present invention, the compounds of formula (II) and formula (III) are reacted in an anhydrous nonpolar organic solvent which should be inert toward the reactants and the desired product, and should have a boiling point sufficiently high to allow heating of the reaction mixture to a desired reaction temperature at which substantial conversion of compounds (II) and (III) to the compound (I) product occurs, as described below. Many such solvents are known, including, but not limited to, tetrahydrofuran, octane, benzene, toluene, and xylene, or mixtures thereof. A preferred solvent is toluene.

The reaction is conducted in the presence of a catalytic amount of a phase transfer catalyst. Such amount may vary considerably, depending upon the concentrations of the reactants and the reaction temperature. In general, the molar ratio of the catalyst to the phthalimide compound of formula (II) ranges from about 0.01:1 to about 0.04:1, preferably from about 0.02:1 to about 0.03:1. Greater amounts of the catalyst do not significantly improve the reaction yield or efficiency and may interfere with recovery procedures, whereas lower concentrations may not provide the desired catalytic effect.

The use of phase transfer catalysts is well known. (See, for example, U.S. Pat. Nos. 4,577,033; 4,554,357; 4,513,141; 4,273,712; and 4,460,778.) Such catalysts effectively catalyze chemical reactions wherein one (or more) reactant is found in one phase of the reaction mixture, whereas the other reactant(s) is found in a different phase of the reaction mixture. The different phases in a reaction mixture may, for example, be aqueous and organic phases, or solid and liquid phases. In the ether-forming reaction of the invention, the alkali metal salt of the compound of formula (III) is insoluble and therefore forms a solid phase, while the compound of formula (II) is soluble in the organic solvent (liquid phase). Many suitable phase transfer catalysts are known, and commonly are quaternary ammonium and phosphonium salts. (See, for example, U.S. Pat. Nos. 4,273,712 and 4,554,357.) Known phase transfer catalysts include the diquaternary ammonium salt bis(tri-n-butyl)-1,6-hexylene diammonium dibromide, tetrapropylammonium bromide, tetrabutylammonium chloride, tetrabutylammonium fluoride, tetrabutylammonium acetate, tetrabutylphosphonium bromide, tetraphenylphosphonium bromide, and many others. A preferred phase transfer catalyst for use in the present invention is tetrabutylammonium bromide.

As used herein, "ether forming conditions" generally include heating the reaction mixture to a temperature sufficiently high to achieve substantial conversion of the reactants of formulae (II) and (III) to the aromatic bis(ether phthalimide) compound of formula (I). In general, this temperature may range from about 40° C. to about 150° C. The temperature advantageously ranges from about 100° C. to about 130° C., preferably from about 105° C. to about 120° C. The reaction is conveniently conducted by heating the mixture to reflux. To avoid deleterious side reactions, the reaction mixture is advantageously maintained under an inert atmosphere and substantially anhydrous conditions. A preferred procedure involves conducting the reaction under a dry nitrogen atmosphere.

In accordance with the present invention, the reaction is initiated by adding the compounds of formulae (II) and (III), and the phase transfer catalyst, to the solvent. The order of addition of the reactants and catalyst may vary. The concentration of the reactants in the solvent may also vary over a fairly wide range. The reaction mixture preferably has high enough concentrations of the reactants so that the reaction proceeds at a satisfactory rate.

The compound of formula (III) is present in the reaction mixture in a stoichiometric molar excess over the compound of formula (II). Two moles of compound (II) react with one mole of compound (III) to produce a compound of formula (I). Therefore, a "stoichiometric molar excess" of a compound of formula (III) in the reaction mixture means that the molar concentration of compound (III) is over half the molar concentration of compound (II). Preferably, the compound of formula (III) is present in the reaction mixture at only a slight stoichiometric excess over the compound of formula (II), to minimize the presence of unreacted, and therefore "wasted", reactant of formula (III) in the reaction mixture after competition of the reaction. In general, the initial concentration of the compound of formula (II) ranges from about 0.1 to about 3.0 molar, preferably from about 1.0 to about 2.0 molar. The initial concentration of the alkali salt of compound of formula (III) generally ranges from about 0.1 to about 2.0 molar, preferably from about 0.6 to about 1.20 molar. The concentrations of the two reactants are chosen to give the desired molar relationship described above.

Thus, the compound of formula (II) is substantially completely used up in the reaction, so that essentially none of the formula (II) phthalimide reactant remains, unreacted, in the reaction mixture after the reaction has gone to completion. This is beneficial because such formula (II) reactants, when present (after the reaction) as unreacted impurities, are often difficult to remove from the reaction mixture. Removal of such impurities is desirable in order to isolate the desired product in pure form, and because certain compounds of formula (II) impart undesirable coloration to the aromatic bis(ether phthalimide) product. In addition, compounds of formula (II) generally are relatively expensive, and it therefore is desirable to minimize the costly "waste" of such compounds that results when a percentage of the compound is left unreacted in the reaction mixture.

The reaction mixture is heated, as described above, until complete. In one embodiment of the invention, the mixture is heated at reflux for about one to about two hours. The reaction may be monitored by high pressure liquid chromatography to detect unreacted compound (II).

Upon completion of the reaction, steps are taken to remove impurities from the reaction mixture. By "impurities" is meant compounds other than the desired product of formula (I). One such step involves the optional addition of a base to the reaction mixture. Suitable bases include those containing alkali metals, such bases including, but not limited to, NaOH, KOH, LiOH, $Na_2CO_3$, $K_2CO_3$ and $Li_2CO_3$. This step is believed to form the alkali metal salts of impurities which are present in the free acid form. Such salts are insoluble in the organic solvent. If any reactant of formula (II) or other solvent soluble impurities are present, they also may be converted to solvent-insoluble salts by base addition. Advantageously, the base is added to the reaction mixture in an amount effective in converting impurities to the salts thereof. Such amounts generally range from a final concentration of from about 0.1% to about 2.0% (w/v), preferably from about 0.2% to about 0.6% (w/v). Following base addition, the reaction mixture may be heated, preferably to between about 80° C. and 115° C. Advantageously, the base is added in dry powdered form to maintain anhydrous conditions in the reaction mixture. Additional organic solvent may be added, if desired. In one embodiment of the invention, powdered NaOH is added to a final concentration of about 0.5% (w/v) and the resulting mixture is heated at reflux for about 15 minutes.

A solid-liquid separation step follows the optional base addition step above or may directly follow completion of the reaction. As described above, this step may comprise filtration. The solid-liquid separation is conducted in an anhydrous nonpolar organic solvent (described above) at a temperature at which the desired product of formula (I) is soluble, while impurities generally are insoluble. Solvent may be added, if necessary, so that the volume of solvent is sufficient to ensure that the desired product remains in solution. The filtration preferably is conducted in toluene at a temperature between about 80° C. and about 105° C. The reaction mixture may be filtered through any suitable known filter material effective in retaining the insoluble salts of impurities while allowing the desired product to flow through the filter into the filtrate. Such materials include, but are not limited to, conventional laboratory filter paper or sintered glass filters, wherein the porosity of the filter ranges from about 1 to about 100 microns, preferably from about 10 to about 50 microns. In one embodiment of the invention, a sintered glass filter funnel, having a porosity of 25–50 microns, is used. The "hot filtration" step is effective in reducing or essentially eliminating sodium nitrite (formed as a by-product when the sodium salt of a compound of formula (III) is reacted with a compound of formula (II) in which $R_3$ is a nitro group), the "monoimide" formed during the reaction and having the formula:

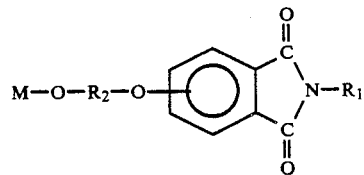

the salts of reactants of formulae (II) and (III), and other impurities, including highly colored impurities, from the filtrate.

Following the solid-liquid separation step, the liquid (e.g., the filtrate) advantageously is extracted with water. The number of extractions (or washes) with water advantageously is kept to a minimum, to minimize physical loss of the product which generally occurs during such water washes. The water extraction removes the phase transfer catalyst from the filtrate into the water, while the desired product remains in the filtrate (the organic solvent.) The quantity and temperature of the water and the number of extractions are sufficient to substantially remove the phase transfer catalyst. In general, one extraction is sufficient. In one embodiment of the invention, the filtrate is extracted twice with an approximately equal volume of distilled water at a temperature of about 70° C. to about 90° C.

After the washing step, the filtrate comprises the desired product in an organic nonpolar solvent. The desired product, the compound of formula (I), is then recovered from the filtrate by any suitable means. Advantageously, the solvent is evaporated, leaving the aromatic bis(ether phthalimide) compound as a dry solid. The method of the invention provides a simple, efficient process for production of aromatic bis(ether phthalimide) compounds of formula (I), including the efficient removal of impurities from the reaction mixture. Maintenance of essentially anhydrous conditions minimizes the formation of additional colored impurities, which have been associated with contact with water in the presence of a base. The solid-liquid separation at elevated temperatures in an organic solvent to remove impurities (as opposed to multiple extractions with water or aqueous solutions which have been used to remove impurities) prevents the loss of product which occurs during such water extractions. The product prepared by the method of the invention is recovered in substantially pure form and in high yield.

The following example is provided to illustrate one embodiment of the invention, and is not to be construed as limiting the scope of the invention described and claimed herein.

EXAMPLE I

The sodium salt of Bisphenol A, a compound of formula (III), having the formula

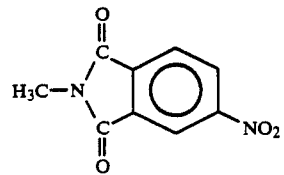

was prepared as follows. A mixture of 40.00% NaOH (2.0000 grams, 0.02000M), Bisphenol A (2.2831 grams, 0.0100M) and 10 mls. of distilled H₂O were heated until the solids were dissolved. Toluene (25 ml) then was added, and the mixture was heated for 6 hours at reflux (about 110° C.) with stirring, with continual azeotropic removal of water during the reaction via a Dean-Stark trap. The resulting solid disodium salt of Bisphenol A was broken into pieces and heated an additional 2 hours at about 110° C. (reflux). Then approximately 15 mls. of toluene was distilled off (after the 2 hour heating step). A reactant of formula (II), N-methyl-4-nitrophthalimide, which has the formula

then was added (3.7127 grams, 0.0180M), along with a phase transfer catalyst, tetrabutylammonium bromide, described above, (0.150 grams, 0.00047M). This mixture (including about 10 mls. of toluene which remained in the flask) was heated to reflux for 1 hour. Next, 0.10 gram of dry powdered NaOH was added, along with 10 mls. of dry (anhydrous) toluene. After heating at reflux for 15 minutes, a 0.2 ml. aliquot of the mixture was removed and analyzed by high pressure liquid chromotography (HPLC). The analysis showed that the mixture comprised 92.595 weight percent of the desired product (Bisphenol A bisimide, described below.) The mixture also comprised impurities which included, among others, the following:

| Impurity | Weight Percent |
| --- | --- |
| formula (II) reactant | 0.488 |
| formula (III) reactant | 0.462 |
| monoimide (described above) | 1.597 |
| "BuBPA" | 1.203 |

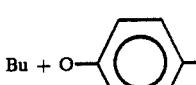

"BuBPA MI" 0.530

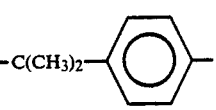

The mixture then was "hot filtered" by pouring it through a 25-50 micron sintered glass filter funnel. The filtration step was completed quickly so that the solvent remained at a temperature high enough that the desired product remained in solution. The solids collected on the filter were washed by pouring about 10 mls. toluene onto the filter. A 0.2 ml. aliquot of the filtrate was analyzed by HPLC. The analysis showed that the filtrate comprised 97.633 weight percent of the desired product. The mixture also comprised the following impurities in the indicated weight percentages:

| Impurity | Weight Percent |
| --- | --- |
| formula (II) reactant | undetectable |
| formula (III) reactant | 0.059 |
| monoimide | 1.415 |
| BuBPA | 0.077 |
| BuBPA MI | 0.619 |

The hot filtration step also reduced the levels of additional unidentified impurities in the mixture.

The filtrate then was diluted with 20 mls. of toluene and extracted with distilled water (2 extractions, 25 mls. each) at 80° C. to remove the phase transfer catalyst. The toluene phase was evaporated to dryness, and 4.72 grams of Bisphenol A bisimide (a compound of formula I) containing about 1.4 weight percent of the monoimide (described above) were recovered. The yield of the desired product was 96.0% based on the N-methyl-4-nitro-phthalimide reactant. The formula of the product is as follows:

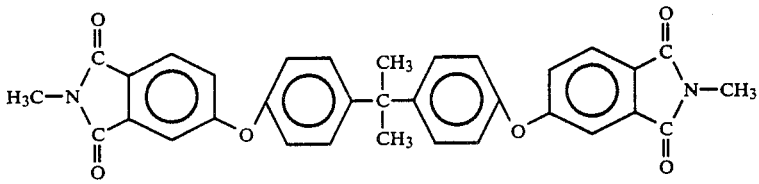

The amounts of a number of impurities, including color-imparting impurities, were effectively reduced after the hot filtration step of the method of the invention. Improved yield of the desired product (based on conversion of the reactant of formula (II)) also was demonstrated.

I claim:

1. A method of synthesizing an aromatic bis(ether phthalimide of the formula (I):

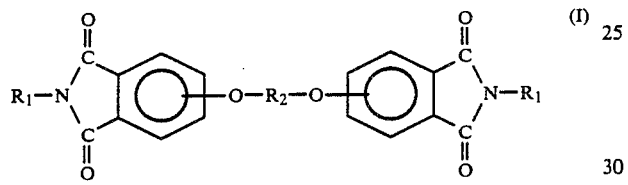

comprising reacting a phthalimide of the formula (II):

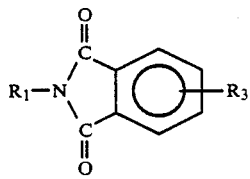

with a stoichiometric molar excess of an alkali metal diphenoxide salt of the formula (III):

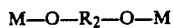

in the presence of a catalytic amount of a phase transfer catalyst, in an anhydrous nonpolar organic solvent under ether-forming conditions, then performing a solid-liquid separation technique on the reaction mixture at a temperature at which the compound of formula (I) is substantially completely soluble while alkali metal salts of impurities are substantially insoluble in said organic solvent, and recovering the compound of formula (I) from the liquid phase, wherein $R_1$ is selected from the group consisting of hydrogen; a lower alkyl group having from 1 to about 10 carbon atoms; and an aromatic hydrocarbon radical or chloro- or bromo-substituted aromatic hydrocarbon radical thereof, having from about 6 to about 20 carbon atoms; $R_2$ is a divalent organic radical selected from the group consisting of:

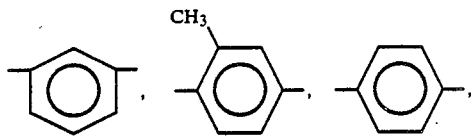

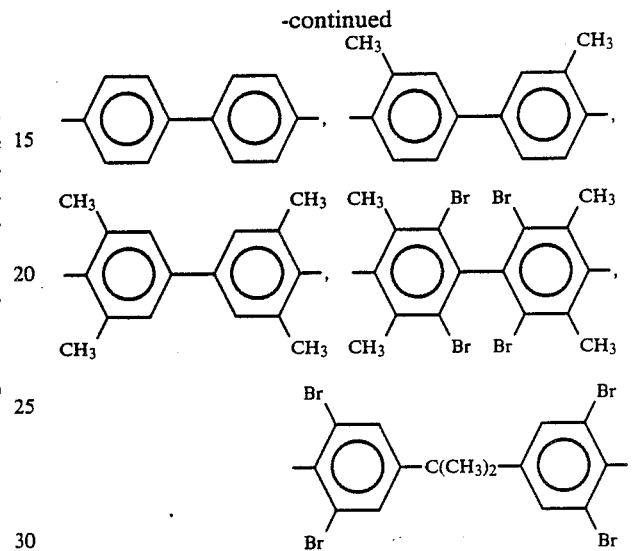

and divalent organic radicals of the general formula:

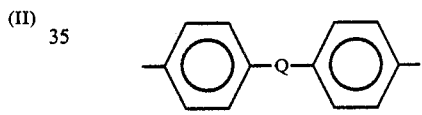

where Q represents a member selected from the class consisting of:

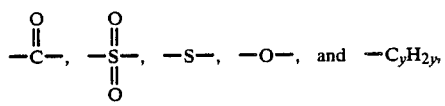

where y is a whole number from 1 to about 5; M is an alkali metal-ion; and $R_3$ is a leaving group.

2. The method of claim 1, wherein $R_1$ is a lower alkyl group having from 1 to about 5 carbon atoms.

3. The method of claim 2, wherein $R_1$ is a methyl group.

4. The method of claim 1, wherein $R_2$ is a divalent organic radical of the formula

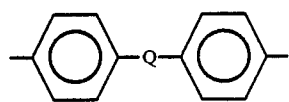

wherein Q is selected from the group consisting of

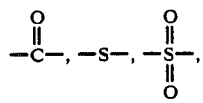

—O—, and —CyH2y— (where y is a whole number from 1 to about 5.)

5. The method of claim 1, wherein R2 is the radical

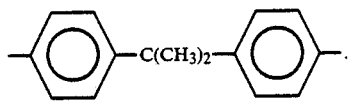

6. The method of claim 1, wherein R3 is selected from the group consisting of a nitro group and a halide atom.

7. The method of claim 1, wherein M is selected from the group consisting of sodium, potassium, and lithium ions.

8. The method of claim 1, wherein said phase transfer catalyst is a quaternary ammonium or phosphonium salt.

9. The method of claim 8, wherein said catalyst is selected from the group consisting of bis(tri-n-butyl)-1,6-hexylene diammonium dibromide, tetrapropylammonium bromide, tetrabutylammonium chloride, tetrabutylammonium fluoride, tetrabutylammonium acetate, tetrabutylphosphonium bromide, and tetraphenylphosphonium bromide.

10. The method of claim 8, wherein said phase transfer catalyst is tetrabutylammonium bromide.

11. The method of claim 8, 9, or 10, wherein the molar ratio of the catalyst to the phthalimide compound of formula (II) is about 0.01:1 to about 0.04:1.

12. The method of claim 11, wherein said molar ratio is about 0.02:1 to about 0.03:1.

13. The method of claim 1, wherein said solvent is selected from the group consisting of tetrahydrofuran, octane, benzene, toluene, xylene, and mixtures thereof.

14. The method of claim 13, wherein said solvent is toluene.

15. The method of claim 1, wherein said ether-forming conditions comprise heating the reaction mixture to a temperature of from about 40° C. to about 150° C. under an inert atmosphere and under substantially anhydrous conditions.

16. The method of claim 15, wherein said reaction mixture is heated to a temperature of from about 100° C. to about 130° C.

17. The method of claim 16, wherein said reaction mixture is heated to reflux.

18. The method of claim 1, wherein the initial concentration of the compound of formula (II) in the reaction mixture ranges from about 0.1 to about 3.0 molar.

19. The method of claim 18, wherein the initial concentration of the compound of formula (III) in the reaction mixture ranges from about 0.1 to about 2.0 molar.

20. The method of claim 18, wherein the initial concentration of the compound of formula (II) in the reaction mixture ranges from about 1.0 to about 2.0 molar.

21. The method of claim 20, wherein the initial concentration of the compound of formula (III) in the reaction mixture ranges from about 0.6 to about 1.2 molar.

22. The method of claim 1, wherein the solid-liquid separation technique comprises filtration at a temperature between about 80° C. and about 105° C., and the compound of formula (I) is recovered from the filtrate.

23. The method of claim 1, wherein, prior to said filtering but following the reaction of said phthalimide with said alkali metal diphenoxide salt, a base containing an alkali metal is added to the reaction mixture in an amount effective in converting impurities to the alkali metal salts thereof.

24. The method of claim 23, wherein said base is selected from the group consisting of NaOH, KOH, LiOH, Na2CO3, K2CO3, and Li2CO3.

25. The method of claim 24, wherein said base is added to the reaction mixture to a final concentration of from about 0.1 to about 2.0% (w/v).

26. The method of claim 25, wherein said base is added to the reaction mixture to a final concentration of from about 0.2 to about 0.6% (w/v).

27. The method of claim 23, wherein, after addition of said base, the reaction mixture is heated to between about 80° C. and about 115° C.

28. The method of claim 27, wherein said base is NaOH which is added to a final concentration of about 0.5% and the reaction mixture then is heated at reflux for about 15 minutes.

29. The method of claim 22, wherein said filtrate is extracted with water under conditions effective in removing the phase transfer catalyst from said filtrate, and the compound of formula (I) then is recovered from said filtrate.

30. The method of claim 22, wherein the compound of formula (I) is recovered from the filtrate by evaporating the solvent therefrom.

31. A method of synthesizing an aromatic bis(ether phthalimide of the formula (I):

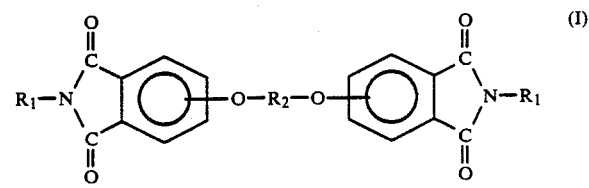

comprising reacting a phthalimide of the formula (II):

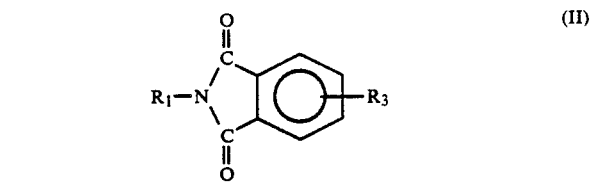

with a stoichiometric molar excess of an alkali metal diphenoxide salt of the formula (III):

in the presence of a catalytic amount of a phase transfer catalyst, in an anhydrous nonpolar organic solvent under ether-forming conditions, then performing a solid-liquid separation technique on the reaction mixture at a temperature between about 80° C. and 105° C. and at which the compound of formula (I) is substantially completely soluble while alkali metal salts of impurities are substantially insoluble in said organic solvent, and recovering the compound of formula (I) from the liquid phase, wherein R1 is selected from the group consisting of hydrogen; a lower alkyl group having from 1 to about 10 carbon atoms; and an aromatic hydrocarbon radical or chloro- or bromo-substituted aromatic hydrocarbon radical thereof, having from about 6 to about 20 carbon atoms; R2 is a divalent organic radical selected from the group consisting of:

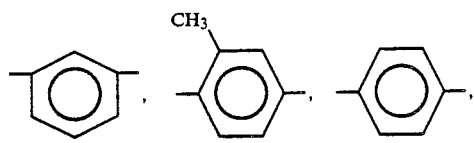
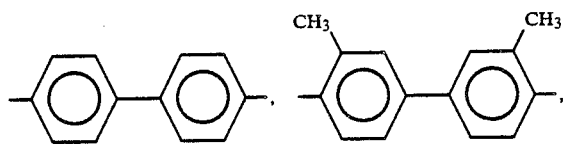
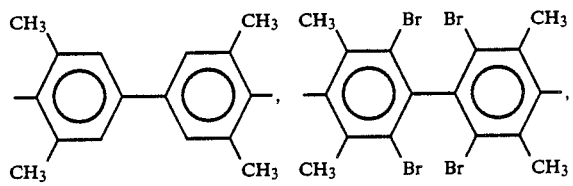
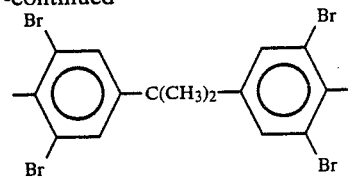
and divalent organic radicals of the general formula:
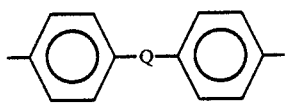
where Q represents a number selected from the class consisting of
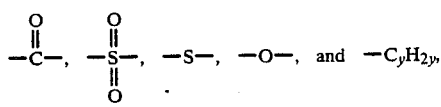
where y is a whole number from 1 to about 5; M is an alkali metal ion; and $R_3$ is a leaving group.
* * * * *